United States Patent
Mirtsch et al.

(10) Patent No.: US 6,221,299 B1
(45) Date of Patent: Apr. 24, 2001

(54) STRUCTURING PROCESS THAT STIFFENS AND PROTECTS THE SURFACE OF THIN MATERIAL WEBS

(76) Inventors: Frank Mirtsch, Kreuzritterstrasse 31, 13465 Berlin; Olaf Büttner, Aachener Strasse 44, 01713 Berlin; Frank Matschiner, Schleiermacherstrasse 8, 06114 Halle, all of (DE)

( * ) Notice: Subject to any disclaimer, the term of this patent is extended or adjusted under 35 U.S.C. 154(b) by 0 days.

(21) Appl. No.: 09/171,505
(22) PCT Filed: Apr. 18, 1996
(86) PCT No.: PCT/EP96/01608
  § 371 Date: Oct. 19, 1998
  § 102(e) Date: Oct. 19, 1998
(87) PCT Pub. No.: WO97/39846
  PCT Pub. Date: Oct. 30, 1997
(51) Int. Cl.⁷ .................. B29C 53/04; B29C 53/08; B29C 69/02; B21D 7/08; B21D 9/10
(52) U.S. Cl. .......... 264/285; 264/295; 264/313; 264/292; 264/320; 264/339; 72/57; 72/196; 72/421; 425/365; 425/392
(58) Field of Search ................ 264/557, 566, 264/230, 285, 295, 313, 319, 339, 322, 284, 286, 287, 280, 294, 505, 506, 292, 320; 425/365, 374, 387.1, 392; 72/57, 421, 196

(56) References Cited

U.S. PATENT DOCUMENTS 3,130,412 * 4/1964 Fox et al. .
3,481,830 * 12/1969 Hanke .
3,667,265 * 6/1972 Zippe ........................... 72/84
4,027,517 * 6/1977 Bodnar ........................ 72/177
4,059,000 * 11/1977 Bodnar ........................ 72/197
4,576,669 * 3/1986 Caputo ....................... 156/145
4,614,632 * 9/1986 Kezuka et al. ............... 264/280
4,842,794 * 6/1989 Hovis et al. ................. 264/145
5,238,642 * 8/1993 Benquet et al. .............. 264/284
5,626,944 * 5/1997 Rasmussen .................. 428/172
5,887,470 * 3/1999 Mirtsch ....................... 72/57

FOREIGN PATENT DOCUMENTS 2557215  6/1977 (DE) .
4311978  4/1994 (DE) .
3587768 10/1994 (DE) .
0441618  8/1991 (EP) .
1283530 12/1961 (FR) .
WO 94/22612 * 10/1994 (WO) .

OTHER PUBLICATIONS

USPTO translation of WO 94/22612, Jun. 1999.*

* cited by examiner

Primary Examiner—Jan H. Silbaugh
Assistant Examiner—Michael I. Poe
(74) Attorney, Agent, or Firm—Nils H. Ljungman & Associates (57) ABSTRACT

The present invention provides a profiling process which allows for the material sheet to be profiled so that the surface is minimally affected and only slight plastic deformation of the material occurs, and yet uniform three-dimensional structuring takes place. Additionally, the present invention allows for an improved inherent stability in the plane of the profiled material sheet to be achieved while only minimally affecting the cross-section.

10 Claims, 6 Drawing Sheets

STRUCTURING PROCESS THAT STIFFENS AND PROTECTS THE SURFACE OF THIN MATERIAL WEBS

FIELD OF THE INVENTION

The invention concerns a process and an apparatus for surface-preserving stiffening profiling of thin material sheets or foils in which curved material sheets or foils are supported on supporting elements and pressurized with excess or negative pressure.

BACKGROUND ART

Numerous deformation methods are known for stiffening thin material sheets and foils by profiling, among them deep-drawing, pressing and rolling with form tools such as molds and shape rolls. The drawback of these deformation technologies is that the mechanical surface pressure strongly plastifies the material sheets and foils to be profiled and degrades their surface quality.

The European patent application 0 441 618 A 1 describes a process in which polyhedral structures such as rhombic and hexagonal profiles are produced with the aid of two embossing rolls. Owing to the strong mechanical deformation, this purely mechanical forming process considerably degrades the surface quality of the materials. U.S. Pat. No. 4,576,669 suggests to feed plastic foil over a roll that carries small cups into which the plastic foil is sucked by vacuum pressure. Thus the cross-section of the foil is reduced, cracks can occur, and the inherent stability of the foil is not noticeably enhanced. Also, a device is known which serves to emboss axial beads into cans by supporting the cans on axial, rigid elements from the inside and pressurizing the outside by means of an elastic roller (DE 35 87 768 T 2). However, the inherent stability of the material furnished with axial beads in this way is insufficient because for geometric reasons beads do not yield multi-dimensional inherent stability. A process in which round, dome shaped structures are impressed in a foil by means of a perforated, cylindrical form tool and an elastic press roller also leads to a reduced cross-section of the foil and does not improve, or only very slightly improves, inherent stability because large regions remain undeformed between the round, dome shaped structures (French application no. 1,283,530).

Furthermore, a process is known in which thin material sheets or foils are profiled dent-like. In the process, the curved thin material sheet or foil is supported by line shaped supporting elements on the inside, and hydraulically pressurized from the outside. Offset quadrangular dent structures result that considerably improve the inherent stability of the material sheet (*Deutsche Offenlegungsschrift* 25 57 215 [Patent Application Open To Public Inspection], German printed patent specification DE 43 11 978). In principle, this dent-profiling process differs from the one described in application no. 0 441 618 A 1 in that not two mechanically acting embossing rollers are required but only a core with line shaped supporting elements on which the material sheet rests and against which it is hydraulically pressed. The curved material sheet which is supported on the inside by supporting elements arranged at intervals (rings or helix) becomes unstable due to the outside pressure. The instability results in multi-dimensional folding, and consequently offset quadrangular dent profiles form in a self-organizing process with the dent troughs evolving by themselves. As the material is only slightly stretched and upset in this process, the surface quality of the material is not degraded, or only very slightly, degraded. However, this offset quadrangular profiled material sheet (see FIG. 2 in DE 43 11 978) has no isotropic inherent stability in the plain because it is flexibly perpendicular to the continuous dent folds, and dimensionally stable parallel to these folds.

An almost isotropic inherent stability is achieved by a process in which hexagonal dent profiles are produced (published international patent application PCT/EP 94/01043, FIG. 5b and 5c). Instead of hydraulic pressure, an unprofiled, elastic cushion or an unprofiled elastomer can be used for pressurization. The supporting elements against which the material sheet is pressed are made of a flexible material which is either fixed or movable on the core. However, the hexagonal structures thus produced are not uniform.

All known profiling processes that use form tools have the essential disadvantages that the material is severely plastified, that in deep-drawing the wall thickness of the material sheet is decreased and the material can tear, that in deep-drawing bearing of the material sheet can occur, and that the surface quality of the material is degraded due to the pressure on the surface by the form tools and the severe plastification. At a given spatial depth of structure these conventional, purely mechanical, profiling methods result in a high degree of plastic deformation of the material which degrades the surface quality of the material.

Another essential drawback of the hydraulic profiling processes described in OS 25 57 215, DE 43 11 978, and PCT/EP 94/01043, is that although the degree of plastic deformation is lower than with the purely mechanical methods and the surface quality of the material is not degraded, the structures produced are not regular. The reasons for that are, among others, inevitable material non-homogeneity, wall thickness tolerances of the material to be processed, and the not absolutely even pressurization of the material sheet.

SUMMARY OF THE INVENTION

This invention provides a profiling process which allows for the material sheet to be profiled so that the surface is minimally affected and only slight plastic deformation of the material occurs, and yet uniform three-dimensional structuring takes place. Additionally, the invention allows for an improved inherent stability in the plane of the profiled material sheet to be achieved while only minimally affecting the cross-section.

According to the present invention, these achievements are made by pressurizing a curved material sheet from the outside via elastic, unstructured elements pressing it against rigid, quadrangular or hexagonal supporting elements which are arranged so that their shapes correspond with the dent folds that evolve by self-organization. This process is basically different from all known, purely mechanical, profiling methods because the dents spring into their final shape in the material sheet and no contact with the mechanical form tool against which they are pressed takes place. The improved inherent stability by dent-profiling results from the formation of dents that adopt their spatial, dimensionally stable dome shape on their own. Experiments have again and again proved this effect. In the process according to the invention, the geometry of the rigid, quadrangular or hexagonal supporting elements corresponds to the dents that evolve by self-organization. In this material-previewing way, regularly arranged structures are produced because by presetting the optimized quadrangular or hexagonal supporting elements the negative effects (non-homogeneity and wall thickness tolerances of the material to be processed, uneven pressurization, etc.) are compensated and the advantages of the surface-preserving and stiffening dent-profiling process with slight plastification of the material are fully made use of.

An embodiment of the invention uses an additional flexible layer between the material sheet to be profiled and the supporting elements to buffer any undesired mechanical imprints made by the supporting elements in a material sheet with a sensitive surface. The resulting dent profiles are flatter with this additional layer than without it. There is another advantage gained by the flexible layer: experiments have shown that when dents form freely dig the indentation process, preferably hexagonal structures evolve if the material sheet is pressed against a core with quadrangular supporting elements and a flexible layer is placed between material sheet and supporting elements. The advantage of this method with respect to engineering and costs is that quadrangular elements are cheaper and simpler to produce than hexagonal ones, and that material sheets with a highly sensitive surface can be structured particularly carefully. However, because, as a consequence of the buffer effect of the flexible layer, the depth of the dents is lower than without the flexibly layer, the inherent stability achieved is also reduced.

Another, embodiment of the invention allows for dent-profiled material sheets or foils to be shaped into spatial shells without complicated form tools being required. To achieve this, material sheets or foils profiled with hexagonal dents are shaped in several dimensions by bending the dent folds of the hexagonal structures deeper where the local radius of curvature of the component is to be increased, and by completely or partly bending them up where the local radius of curvature of the component is to be flatter. Just slight plastification of the material occurs in this bending of the structure folds.

The invention is explained by means of an embodiment in the attached drawing and described in detail in the following. Further advantageous design features resulting from the invention will become apparent in the following description.

BRIEF DESCRIPTION OF THE DRAWINGS

FIG. 9, is an axial cross-section).

FIG. 10 and 11, are diagrammatic views of a dent-profiled material sheet (splint) for confining and supporting two bones (FIG. 10, is an axial cross-section; FIG. 11, is a radial crosssection).

DETAILED DESCRIPTION OF THE INVENTION

Figure 1:
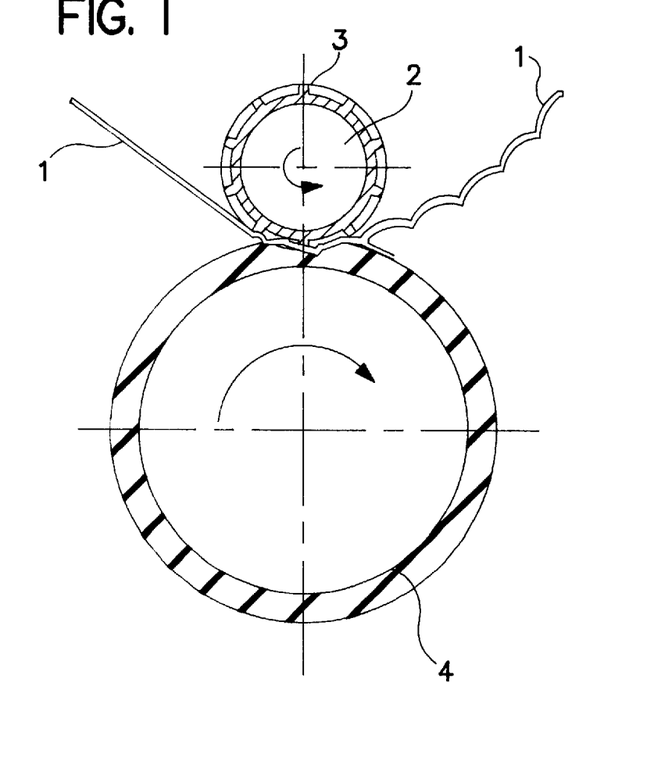
FIGS. 1 and 1A, diagrammatic views of the design of a device for manufacturing material sheets or foils using a roller on which supporting elements are arranged and a flexible press roller (radial cross-section).
Figure 1A:
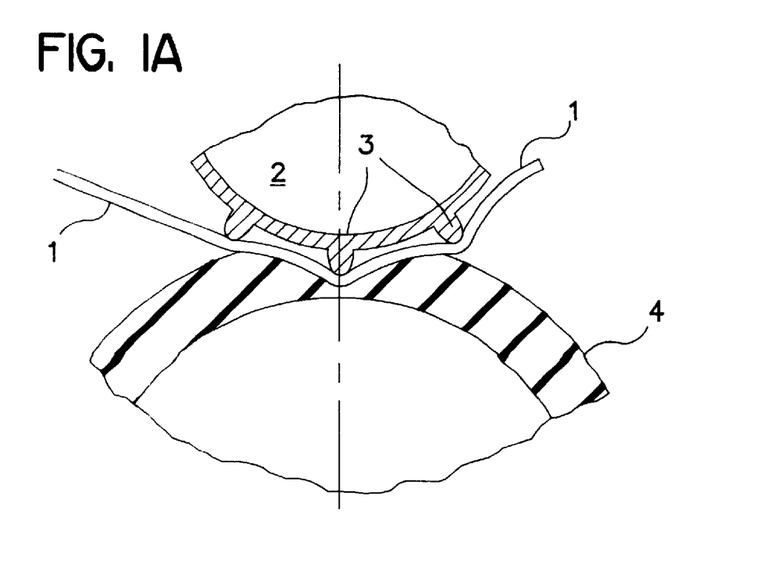

The device depicted in FIGS. 1 and 1A shows the basic design of a device for manufacturing dent-profiled material sheets or foils. The material sheet 1 is fed around the roller 2 on which the supporting elements 3 are arranged, and pressed against the supporting elements 3 by the flexible press roller 4. The pressure put on the curved material sheet 1 by the flexible press roller 4 results in indentation of the material sheet 1 between the supporting elements 3, by which process the dents spring into their final shape without the dent troughs being touched by the mechanical form.

Figure 2:
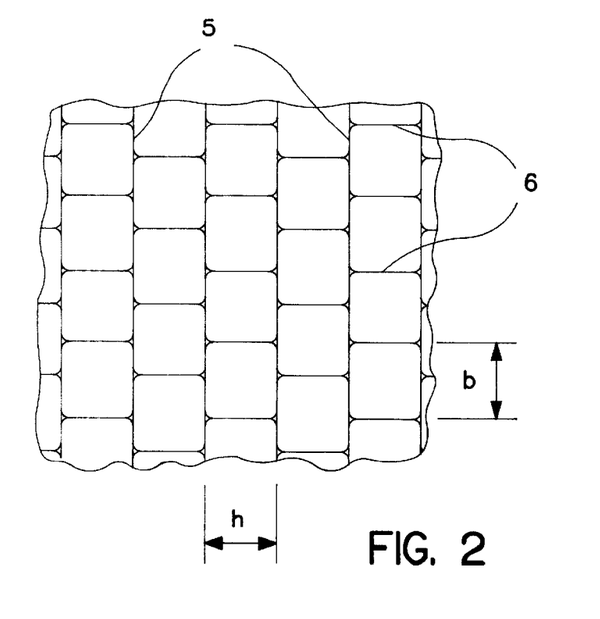
FIG. 2, illustrates a dent structure produced by a device according to FIGS. 1 and 1A, where the device is equipped with offset quadrangular supporting elements.
Figure 3:
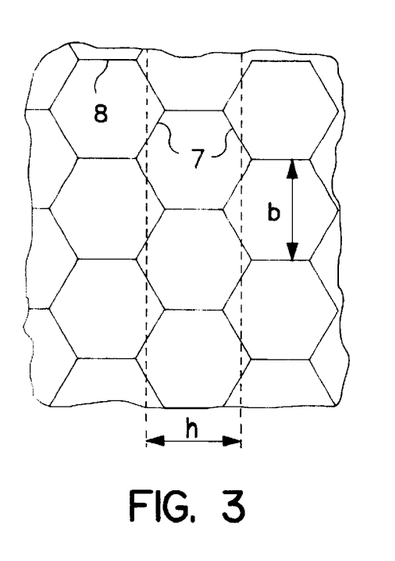
FIG. 3 and 4, illustrates two dent structures produced by a device according to FIGS. 1 and 1A, where the device is equipped with two different hexagonal supporting elements.
Figure 4:
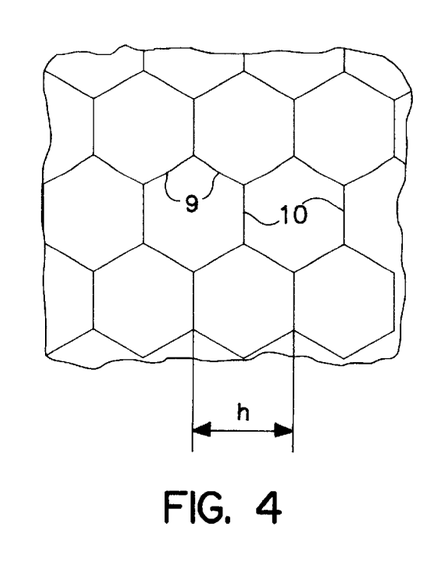

FIG. 2, 3, and 4 depict unwound dent-profiled material sheets produced by means of a device according to FIGS. 1 and 1A. FIG. 2 depicts offset quadrangles resulting from the dent folds 5 (in material sheet feed direction) at a distance h between each other and the dent folds 6 (perpendicular to material sheet feed direction) at a distance b between each other.

FIGS. 3 and 4 depict aspects of two alternative arrangements of hexagonal structures. In FIG. 3, the dent folds 7 (in material sheet feed direction) are zigzag shaped and are at a distance h between each other. The dent folds 8 (perpendicular to material sheet feed direction) are at a distance b between each other. In FIG. 4, the dent folds 9 (transverse to material sheet feed direction) are zigzag shaped. The dent folds 10 (in material sheet feed direction) are at a distance h between each other.

Figure 5:
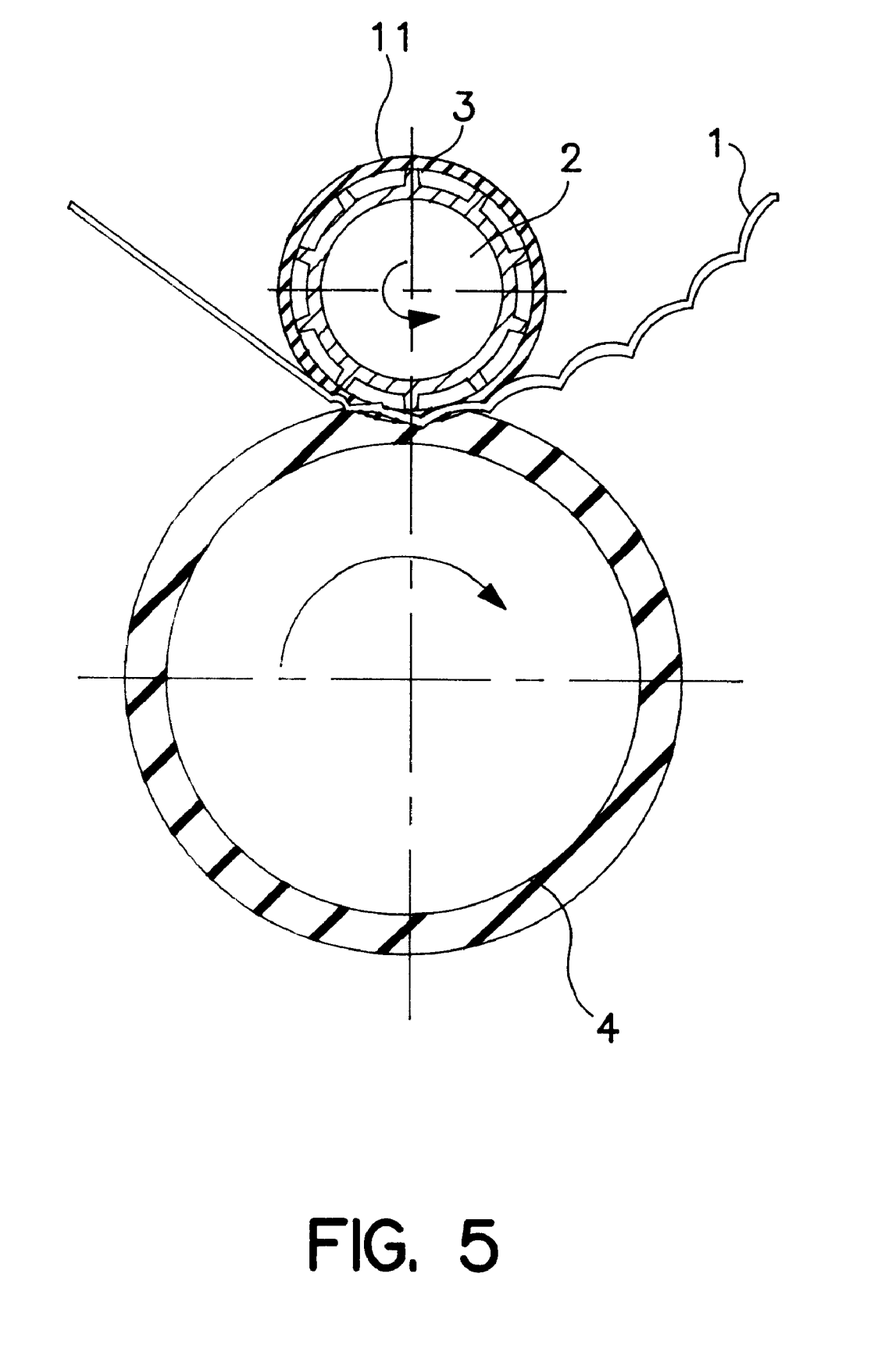
FIG. 5, is a diagrammatic view of the design of a device for manufacturing dent-profiled material sheets by means of a roller on which supporting elements are arranged, a flexible press roller, and an additional flexible layer.

FIG. 5 shows the schematic design of a device for manufacturing dent-profiled material sheets or foils by means of a flexible press roller 4 and a roller 2 on which supporting elements 3 are arranged that are covered by an additional flexible material sheet 11. Thus undesired mechanical imprints caused by possible irregularities of the supporting contours 3 are equalized.

Figure 6:
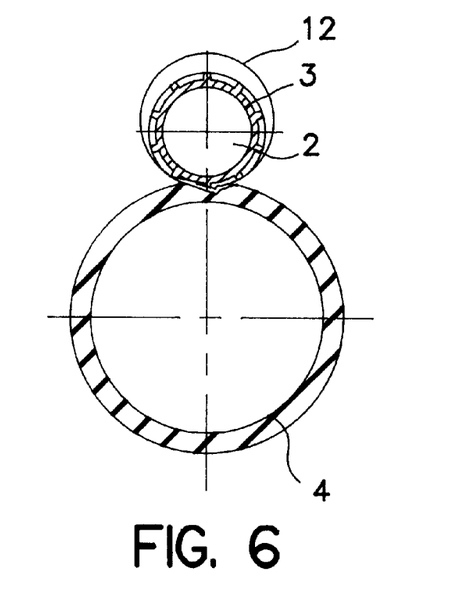
FIG. 6, is a diagrammatic view of the design of a device for manufacturing dent-profiled cans by means of a roller on which supporting elements are arranged and a flexible press roller (radial cross-section).
Figure 7:
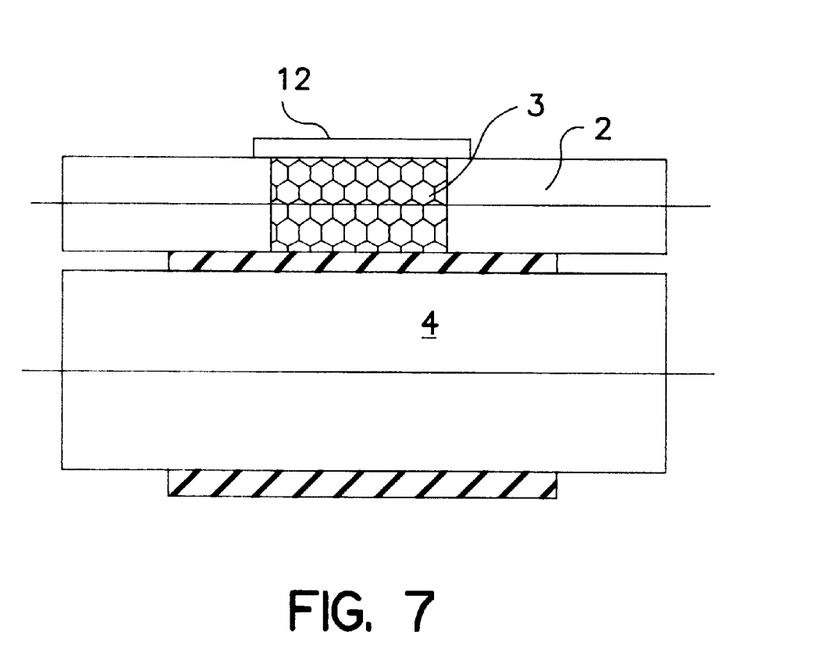
FIG. 7, is a diagrammatic view of the design of a device for manufacturing dent-profiled cans by means of a roller on which supporting elements are arranged (axial aspect) and a flexible press roller (axial cross-section).

FIGS. 6 and 7 schematically depict the manufacture of dent-profiled cans or thin-walled cylinders. FIG. 6 depicts the radial cross-section of the device with the roller 2 on which the supporting elements 3 are arranged, the flexible press roller 4, and the cylindrical can body or cylindrical wall 12. FIG. 7 depicts the components mentioned in axial view.

Figure 8:
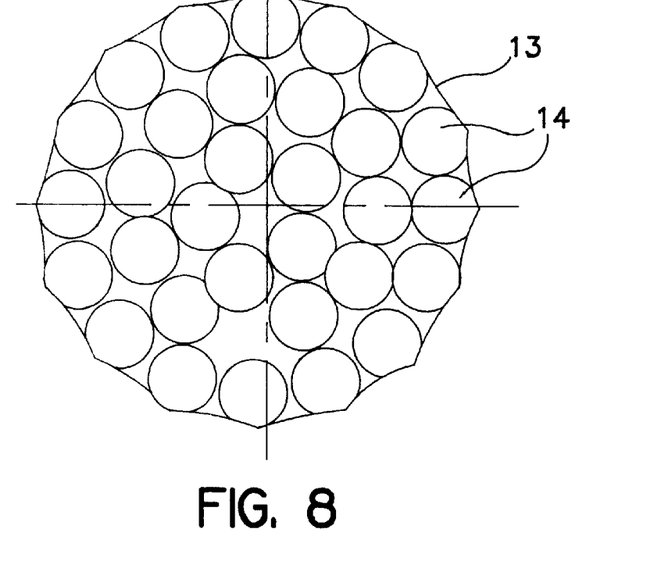
FIG. 8 and 9, are diagrammatic view of a dent-profiled cylindrical container with globular tower packing (FIG. 8, is a radial cross-section.
Figure 9:
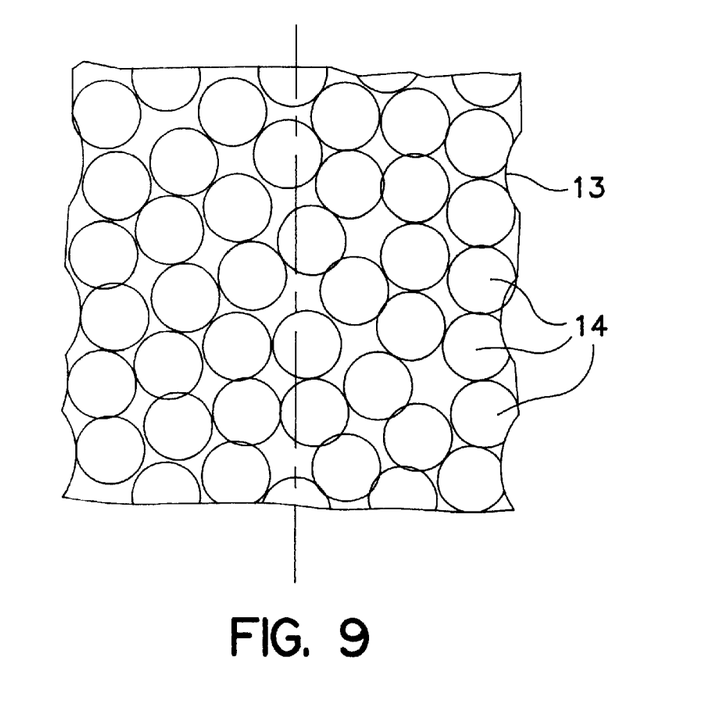

FIGS. 8 and 9 schemaically depict the radial cross-section (FIG. 8) and the axial cross-section (FIG. 9) of a dent-profiled cylindrical container 13 filled with tower packing 14. The dent structures of the container wall 13 are adapted to the curvatures of the balls of the tower packing 14 so that the free cross-section of flow between the balls 14 close to the wall and the dent-profiled container wall 13 is low.

Figure 10:
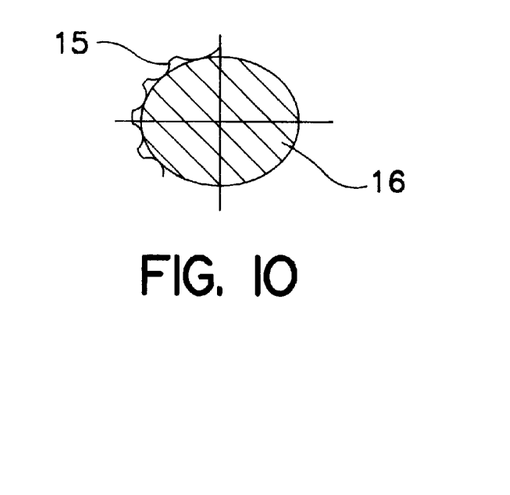
Figure 11:
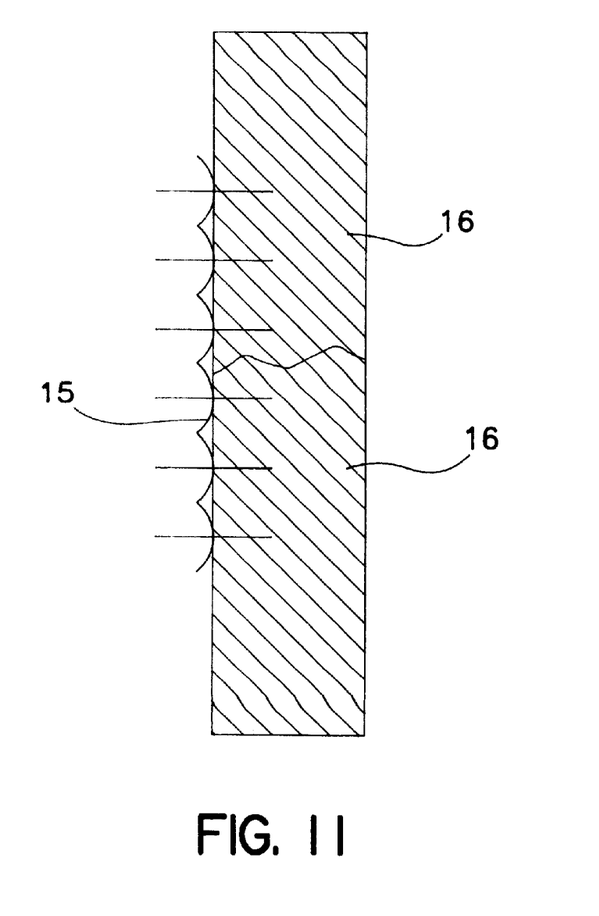

In FIGS. 10 and 11, the radial cross-section (FIG. 10) and the axial cross-section (FIG. 11) of a dent-profiled material sheet 15 which confines and splints two pieces of bone 16 is depicted schematically. The shell shaped dent-profiled material sheet 15 is bent around the pieces of bone 16 and touches the two pieces of bone only with the troughs of its dents. Thus the periost surrounding the bone is highly stressed only at the small contact surfaces between the dent troughs and the bone. In between these contact surfaces the periost continues to be supplied with blood and consequently does not die off. Additionally, the shell shape dent-profiled splint has a higher inherent stability than the conventional smooth splints because, compared to a non-profiled splint of the same material and with the same dimensions, it possesses better flexural strength in radial direction and higher elasticity in the direction of the bone. So the dent-profiled splint adjusts better to the physical properties of the bone than a conventional smooth splint.

What is claimed is:

1. A process for stiffening profiling of thin materials and foils in which a curved material or foil is supported by rigid quadrangular or hexagonal supporting elements arranged on a mechanical forming tool and pressurized against said supporting elements, wherein said curved material or foil is pressurized on the side opposite said supporting elements, by an elastic flexible element so that said material or foil is pressurized in its curvature wherein dent folds which correspond to the shape of said supporting elements evolve by themselves in said material or foil by said dent folds springing and evolving into their final shape in said material or foil by partly or completely bending dent troughs without said dent troughs associated with said dent folds being touched by said mechanical forming tool, thereby producing a stiffened thin material or foil.

2. The process according to claim 1 wherein an additional flexible layer is located between the supporting elements and the material to be profiled.

3. A process for stiffening profiling a thin material to form a curved material, said process comprising the steps of:

equipping a roller with rigid supporting elements;

feeding said thin material between said roller and a flexible press roller such that said thin material is supported by said rigid supporting elements; and applying pressure to said thin material against said rigid supporting elements using said flexible press roller, thus pressing said material against said rigid supporting elements, wherein dent folds having a shape corresponding to said supporting elements, thereby evolve by themselves in said thin material by said dent folds springing and evolving into their final shape by partly or completely bending dent troughs without dent troughs associated with said folds being touched by said roller with rigid supporting elements and wherein a stiffened thin curved material is produced.

4. The process according to claim 3, wherein said process comprises a surface preserving process, and wherein said elastic flexible element comprises an elastic unprofiled element.

5. The process of claim 3 wherein said supporting elements are quadrangular supporting elements.

6. The process of claim 3 wherein said supporting elements are hexagonal supporting elements.

7. A process for stiffening profiling a thin, curved material or foil while preserving a surface of said thin material or foil, said process comprising the steps of:

equipping a roller with rigid supporting elements;

covering said rigid supporting elements by a flexible layer;

feeding said thin, curved material between said roller and a flexible unprofiled press roller such that said thin, curved material is supported by said rigid supporting elements and said flexible layer; and pressurizing said thin material against said rigid supporting elements and said flexible layer by said flexible unprofiled roller;

wherein dent folds having a shape corresponding to said supporting elements evolve by themselves in said material or foil by said dent folds springing and evolving into their final share in said material or foil by partly or completely bending dent troughs without said dent troughs associated with said dent folds being touched by said roller with rigid supporting elements, thereby producing a stiffened thin material or foil.

8. The process of claim 7 wherein said supporting elements are quadrangular supporting elements.

9. The process of claim 7 wherein said supporting elements are hexagonal supporting elements.

10. The process according to claim 7, wherein said supporting elements are quadrangular and said shapes formed in said thin material or foil are hexagonal.

* * * * *

UNITED STATES PATENT AND TRADEMARK OFFICE
CERTIFICATE OF CORRECTION

PATENT NO.    : 6,221,299 B1
DATED         : April 24, 2001
INVENTOR(S)   : Frank Mirtsch, Olaf Buttner and Frank Matschiner It is certified that error appears in the above-identified patent and that said Letters Patent is hereby corrected as shown below:

Column 2,
Line 19, after 'deep-drawing' delete "bearing" and substitute -- earing --.
Line 62, after 'this' delete "material-previewing" and substitute -- material-preserving --.

Column 3,
Line 11, after 'freely' delete "dig" and substitute -- during --.
Line 22, after the first occurrence of 'the' delete "flexibly" and substitute -- flexible --.
Line 49, after '4,' delete "illustrates" and substitute -- illustrate --.
Line 65, after 'diagrammatic' delete "view" and substitute -- views --.

Column 4,
Line 4, delete "crossection)," and substitute -- cross-section). --.
Line 49, after '9' delete "schemaically" and substitute -- schematically --.

Signed and Sealed this

Sixteenth Day of April, 2002

Attest:

JAMES E. ROGAN
Director of the United States Patent and Trademark Office

Attesting Officer